United States Patent
Cao et al.

(10) Patent No.: US 12,318,252 B2
(45) Date of Patent: Jun. 3, 2025

(54) COMBINED ULTRASONIC AND DIRECT VISUAL HYSTEROSCOPE

(71) Applicant: FemDx Medsystems, Inc., Santa Clara, CA (US)

(72) Inventors: Pei-Jie Cao, Newark, CA (US); Albert K. Chin, Palo Alto, CA (US); Xi Francis, Palo Alto, CA (US)

(73) Assignee: FEMDX MEDSYSTEMS, INC., Santa Clara, CA (US)

(*) Notice: Subject to any disclaimer, the term of this patent is extended or adjusted under 35 U.S.C. 154(b) by 74 days.

(21) Appl. No.: 17/942,603

(22) Filed: Sep. 12, 2022

(65) Prior Publication Data
US 2023/0200780 A1    Jun. 29, 2023

Related U.S. Application Data

(60) Provisional application No. 63/243,374, filed on Sep. 13, 2021.

(51) Int. Cl.
*A61B 1/00*    (2006.01)
*A61B 1/018*    (2006.01)
(Continued)

(52) U.S. Cl.
CPC ........ *A61B 8/4416* (2013.01); *A61B 1/00096* (2013.01); *A61B 1/018* (2013.01);
(Continued)

(58) Field of Classification Search
CPC ... A61B 8/4416; A61B 1/00096; A61B 1/018; A61B 1/051; A61B 1/303; A61B 8/12;
(Continued)

(56) References Cited

U.S. PATENT DOCUMENTS

| 4,462,408 A | 7/1984 | Silverstein et al. |
| 5,596,989 A * | 1/1997 | Morita ............... G01N 29/2456 600/463 |

(Continued)

FOREIGN PATENT DOCUMENTS

| CN | 110753521 A | 2/2020 |
| JP | S5673804 U | 6/1981 |

(Continued)

OTHER PUBLICATIONS

PCT/US2021/034100 International Search Report and Written Opinion of the International Searching Authority dated Oct. 28, 2021.
(Continued)

*Primary Examiner* — Amal Aly Farag
(74) *Attorney, Agent, or Firm* — WILSON SONSINI GOODRICH & ROSATI

(57) ABSTRACT

An interventional hysteroscope includes a cannula, an optical imaging element, an ultrasonic imaging element and a treatment element, such as an ablation needle. The cannula has a distal end, a proximal end, and a longitudinal axis therebetween, and the optical imaging element is disposed at the distal end of the cannula. The ultrasonic imaging element is also disposed at the distal end of the cannula and is configured to image along a laterally oriented image path. The treatment element is configured to be deployed from the cannula along a laterally oriented treatment path, and the imaging path and the treatment path intersect at an intersectional location spaced laterally away from the cannula. A display is configured to present both an optical image from the optical imaging element and an ultrasonic image from the ultrasonic imaging element and to present a marker on the ultrasonic image at a location corresponding to the intersectional location.

18 Claims, 8 Drawing Sheets

(51) Int. Cl.
*A61B 1/05* (2006.01)
*A61B 1/303* (2006.01)
*A61B 8/00* (2006.01)
*A61B 8/12* (2006.01)
*A61B 17/34* (2006.01)
*A61B 18/00* (2006.01)
*A61B 18/14* (2006.01)

(52) U.S. Cl.
CPC .............. *A61B 1/051* (2013.01); *A61B 1/303* (2013.01); *A61B 8/12* (2013.01); *A61B 8/463* (2013.01); *A61B 18/1477* (2013.01); *A61B 2017/3413* (2013.01); *A61B 2018/00559* (2013.01); *A61B 2018/00577* (2013.01); *A61B 2018/00982* (2013.01)

(58) Field of Classification Search
CPC ................ A61B 8/463; A61B 18/1477; A61B 2017/3413; A61B 2018/00559; A61B 2018/00577; A61B 2018/00982
See application file for complete search history.

(56) References Cited

U.S. PATENT DOCUMENTS

| | | | |
|---|---|---|---|
| 5,935,098 | A | 8/1999 | Blaisdell et al. |
| 7,678,106 | B2 * | 3/2010 | Lee ........................ A61B 90/36 606/41 |
| 11,602,269 | B2 | 3/2023 | Chin et al. |
| 2004/0030268 | A1 * | 2/2004 | Weng ........................ A61N 7/00 601/2 |
| 2004/0220478 | A1 * | 11/2004 | Wallace ............... A61B 1/0607 600/109 |
| 2011/0098530 | A1 * | 4/2011 | Yamane ................. A61B 1/042 600/109 |
| 2015/0351729 | A1 | 12/2015 | Chin et al. |
| 2016/0287232 | A1 | 10/2016 | Chao et al. |
| 2017/0245878 | A1 | 8/2017 | Aljuri et al. |
| 2017/0258392 | A1 | 9/2017 | Skieller et al. |
| 2019/0133696 | A1 * | 5/2019 | Spero ..................... A61B 8/463 |
| 2021/0059749 | A1 * | 3/2021 | Sharma .............. A61B 18/1492 |
| 2021/0169312 | A1 * | 6/2021 | Morimoto .......... A61B 1/00096 |
| 2021/0187261 | A1 * | 6/2021 | Murdeshwar ...... A61B 17/3478 |
| 2021/0369094 | A1 | 12/2021 | Chin et al. |
| 2022/0031377 | A1 * | 2/2022 | Ransbury ............... A61B 1/063 |
| 2023/0200780 | A1 | 6/2023 | Cao et al. |
| 2023/0309812 | A1 | 10/2023 | Chin et al. |

FOREIGN PATENT DOCUMENTS

| | | |
|---|---|---|
| JP | H0397431 A | 4/1991 |
| JP | 2014507986 A | 4/2014 |
| JP | 2014519925 A | 8/2014 |
| JP | 2014217552 A | 11/2014 |
| JP | 2018517452 A | 7/2018 |
| JP | 2019511266 A | 4/2019 |
| WO | WO-2013137372 A1 | 9/2013 |
| WO | WO-2014057813 A1 | 4/2014 |
| WO | WO-2017205646 A1 | 11/2017 |
| WO | WO-2019049159 A1 | 3/2019 |
| WO | WO-2019191705 A1 | 10/2019 |
| WO | WO-2021242779 | 12/2021 |

OTHER PUBLICATIONS

U.S. Appl. No. 16/882,971 Notice of Allowance dated Feb. 1, 2023.
U.S. Appl. No. 16/882,971 Office Action dated Dec. 7, 2022.
Acquire: Endoscopic Ultrasound Fine Needle Biopsy Device. Boston Scientific. Mar. 2017. Retrieved Jun. 21, 2024 at URL: https://www.bostonscientific.com/content/dam/bostonscientific/endo/portfolio-group/Acquire-Biospy-FNB-Needle/acquire-product-brochure.pdf. pp. 1-4.
EP2021813009.4 Partial European Search Report dated May 21, 2024.
Fuccio, et al. Forward-viewing linear echoendoscope: a new option in the endoscopic ultrasound armamentarium (with video). Journal of Hepato-Biliary-Pancreatic Sciences 22(1):27-34 (2015). Published online Oct. 23, 2014.
EP21813009.4 Extended European Search Report dated Aug. 12, 2024.

* cited by examiner

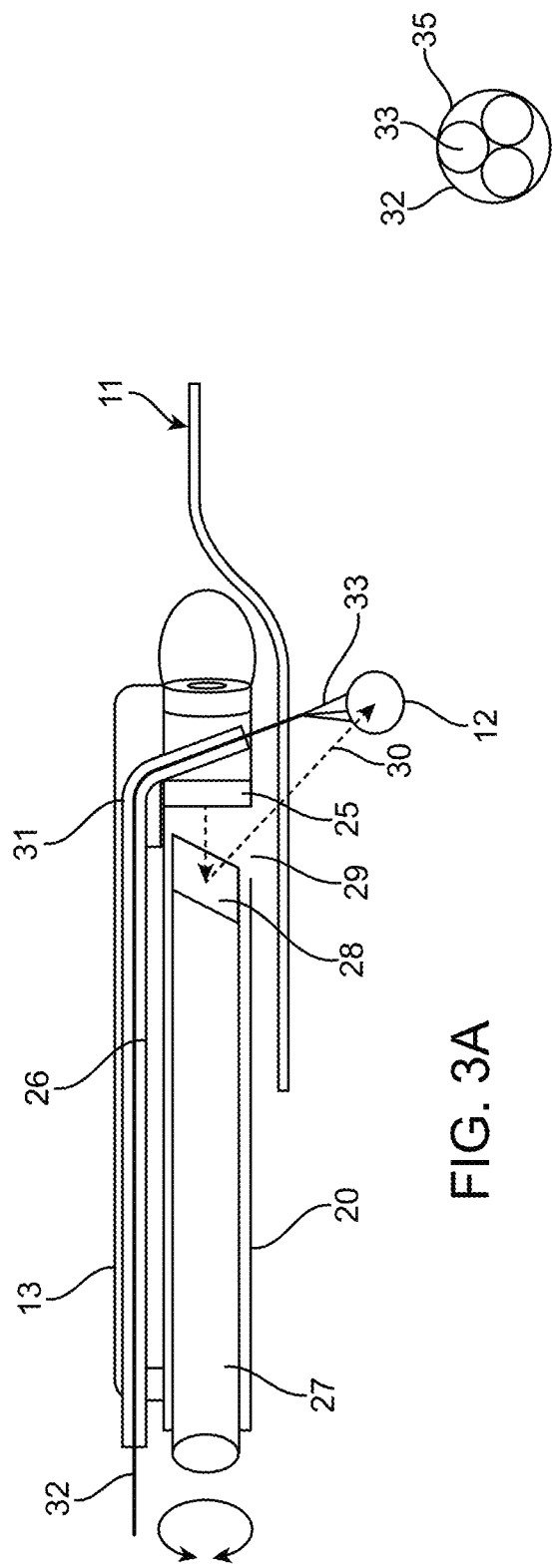
FIG. 3A
FIG. 3B
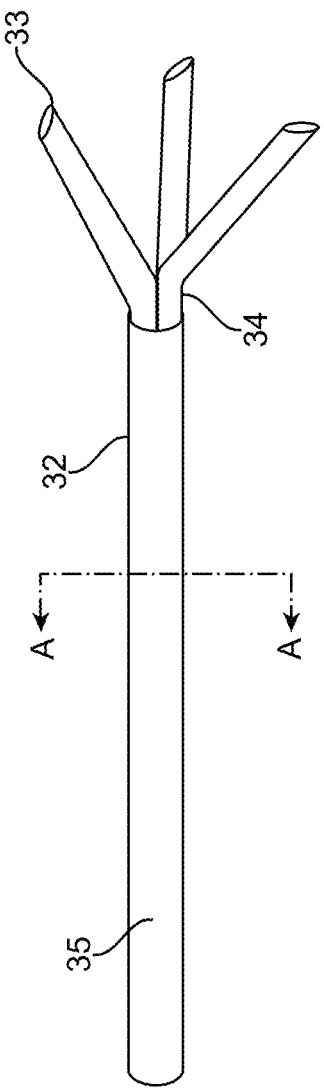
Section A-A
FIG. 3C

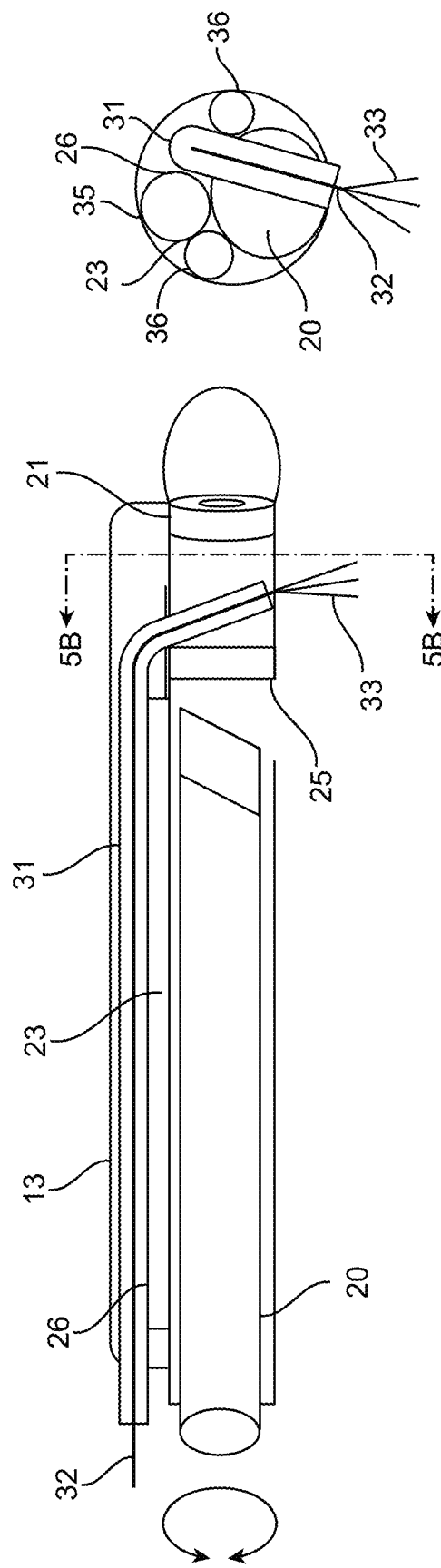

COMBINED ULTRASONIC AND DIRECT VISUAL HYSTEROSCOPE

CROSS-REFERENCE TO RELATED APPLICATIONS

This application claims the benefit of U.S. Provisional No. 63/243,374, filed Sep. 13, 2021, the entire content of which is incorporated herein by reference.

FIELD OF THE INVENTION

This disclosure relates generally to devices and methods for diagnosing and treating abnormalities of the uterus, using a hysteroscope with combined direct visual and ultrasonic images simultaneously displayed on a video monitor, and incorporating a needle that may be advanced distal to the tip of the hysteroscope to intersect with the emitted ultrasound beam. An indicator dot is present on the ultrasonic video display to indicate the point of intersection of the ultrasound beam with the tip of the extended needle. More specifically, combined direct visual and ultrasonic imaging allows a physician to evaluate and treat both surface endometrial lesions as well as submucosal abnormalities with a single device.

BACKGROUND OF THE INVENTION

Uterine abnormalities are commonplace and may lead to abnormal uterine bleeding, pain, fatigue, and infertility. Leiomyomas or fibroids are benign tumors in the uterus that occur in approximately 70% of women by age 50. The average affected uterus contains six to seven fibroids. The most common type of fibroid is intramural, within the muscular wall of the uterus. The fibroid may also be subserosal on the outside of the uterus. Intramural and subserosal fibroids account for 95% of uterine fibroids. The remaining 5% are submucosal, located in the myometrium or middle muscle layer of the uterus. Medication such as hormonal therapy may be used to control the symptoms of fibroids. The most frequent treatment for large or symptomatic fibroids is hysterectomy, i.e., surgical removal of the uterus. Approximately 200,000 hysterectomies are performed annually in the United States for treatment of uterine fibroids.

Non-surgical treatments of uterine fibroids include hysteroscopic myomectomy, an outpatient procedure utilizing instruments inserted through a hysteroscope to shave away the fibroid. This procedure is only applicable to patients with submucosal fibroids that extend from the uterine wall into the uterine cavity. Radiofrequency ablation of uterine fibroids may also be performed via a needle advanced through a hysteroscope that conducts radiofrequency energy into the fibroid, leading to its obliteration. Hysteroscopic myomectomy and hysteroscopic radiofrequency ablation are amenable to patients with submucosal fibroids that extend into the uterine cavity. Submucosal fibroids account for approximately 5% of uterine fibroids. Most fibroids are intramural or subserosal, and not endoscopically visible in the uterine cavity. An intrauterine ultrasound device is available to locate fibroids and deliver radiofrequency energy to fibroids to reduce their size and decrease patient symptoms. This device does not incorporate direct visualization, and it is unable to evaluate the surface morphology of the endometrium, the inner surface of the uterus.

It would be desirable to have an intrauterine device that provides simultaneous real time direct visualization and ultrasonic visualization for full diagnostic capability. Additionally, it would be desirable to provide the uterine visualization device with a radiofrequency ablation needle that may be advanced out of the device into intersection with the ultrasound beam, with the point of intersection indicated on the ultrasound video monitor image.

SUMMARY OF THE INVENTION

The combined ultrasonic and direct visual hysteroscope is a semi-rigid cannula with an outer diameter of approximately 5 mm. The cannula contains multiple internal lumens that accommodate: (1) a CMOS chip endoscope with its distal end covered by a transparent solid spherical tip; (2) an ultrasound source that scans tissue inferior to the cannula; (3) a guide channel angled inferiorly in the distal portion of the cannula to direct a super-elastic needle into tissue in intersection with the ultrasound beam; (4) fluid irrigation and fluid evacuation channels; and (5) a working channel for an additional operating instrument. A single lumen that measures 3 mm in diameter lies in the inferior aspect of the cannula, and this lumen accommodates both the CMOS chip and the ultrasound transducer. The CMOS chip is positioned at the distal end of the 3 mm lumen and directed to view outward from the cannula. A solid optically clear polymeric spherical lens is bonded to the surface of the CMOS chip and protrudes distal to the CMOS chip. This spherical lens preserves the visual image upon tissue contact, in contrast to conventional fiberoptic or CMOS chip endoscopes that present a blurry image upon contact with tissue or bodily fluids. Conventional hysteroscopes require the infusion of saline irrigation to distend the uterus and form a viewing cavity, whereas the spherical lens tipped CMOS endoscope provides visualization of the endometrium with both the presence and absence of uterine distention media.

Placement of both the CMOS sensor and the ultrasound transducer in a single lumen allows the cannula to achieve a small 5 mm profile. A small cannula profile is important in facilitating entry through the patient's cervix without the need for painful cervical dilation and additional local anesthesia such as a paracervical block. The CMOS sensor and the ultrasound transducer coexist in a common lumen, providing continuous simultaneous direct visual and ultrasonic imaging. The CMOS chip is positioned at the distal end of the 3 mm cannula lumen and directed forward to view out into the uterine cavity. The ultrasound transducer is positioned proximal to the CMOS chip in the 3 mm lumen and faces backwards to view towards the proximal end of the device. A 5 mm to 10 mm long window is cut out in the inferior aspect of the cannula immediately proximal to the ultrasound transducer. A rotating rod with an angled distal mirror surface lies within the cutout window in the cannula. The ultrasound signal from the transducer reflects off the mirror surface and out the window to intersect with uterine tissue below and slightly in front of the cannula tip. The CMOS chip endoscope delivers a view of the endometrial surface of the uterus, while the ultrasound imager yields a view of structures deep to the endometrium. The handle of the device contains a video monitor that displays both images simultaneously, allowing the physician to evaluate both uterine endometrial morphology as well as intramural structures. The device handle also houses the small electric motor that rotates the mirrored rod, electronic control boards for the CMOS chip endoscope and the ultrasound transducer, the light source for the CMOS endoscope, and a battery to power the device. The entire device is disposed after a single use, to avoid the potential for infection due to suboptimal instrument sanitization between use on multiple patients, and to avoid the inconvenience and cost of maintaining and storing conventional endoscopic video systems. Current endoscopic video systems consist of large pieces of capital equipment that include a CCD chip camera with its control box, a light source with a fiberoptic light cable, and a large video monitor that is viewed from a distance. The handheld device described herein allows the physician to view the endoscopic and ultrasonic intra-uterine images while also viewing patient surface anatomy at the site of device insertion, enhancing instrument control during the procedure. With current endoscopic equipment, the physician must turn her or his head away from the instrument insertion site to view a video image remote from the patient situated on the examination table.

An instrument lumen that may accommodate 1 mm diameter instruments such as graspers or biopsy forceps lies centrally immediately superior to the channel housing the endoscope and ultrasound units. Lateral to the instrument lumen is a channel that houses a tissue ablation element. The ablation channel contains a distal angled section that passes through the endoscopic lumen in-between the CMOS chip and the ultrasound transducer and exits the inferior aspect of the cannula. The tissue ablation element may be a bundle of three or more needles formed of an electrically conductive super-elastic metal such as Nitinol. Upon advancement through the angled ablation channel, the needle extends in a predetermined path that intersects the ultrasonic beam. In addition, the distal portion of the needles splay out from the central axis of the bundle to enter the intramural fibroid in a spaced out fashion, to disperse the ablation energy to a wider lesion area. The intersection of the needle entry area with the fibroid is indicated by a bright dot on the ultrasonic video image displayed on the video monitor. During a procedure to ablate an intramural fibroid, the physician may angle the cannula to position the bright dot on the ultrasonic image of the fibroid, and upon advancement, the ablation needles will enter the fibroid in a targeted fashion. In an alternative embodiment, the tissue ablation element may be a single super-elastic metal needle that may be inserted multiple times into a broad based fibroid under ultrasonic guidance to perform the ablation.

BRIEF DESCRIPTION OF THE DRAWINGS

FIG. 3A-3C depict the configuration of the multiple pronged ablation needle element in the combined ultrasonic and visual hysteroscope.

FIGS. 5A and 5B shows the configuration of the multiple channels incorporated in the combined ultrasonic and visual hysteroscope cannula.

DETAILED DESCRIPTION OF THE DRAWINGS

Figure 1B:
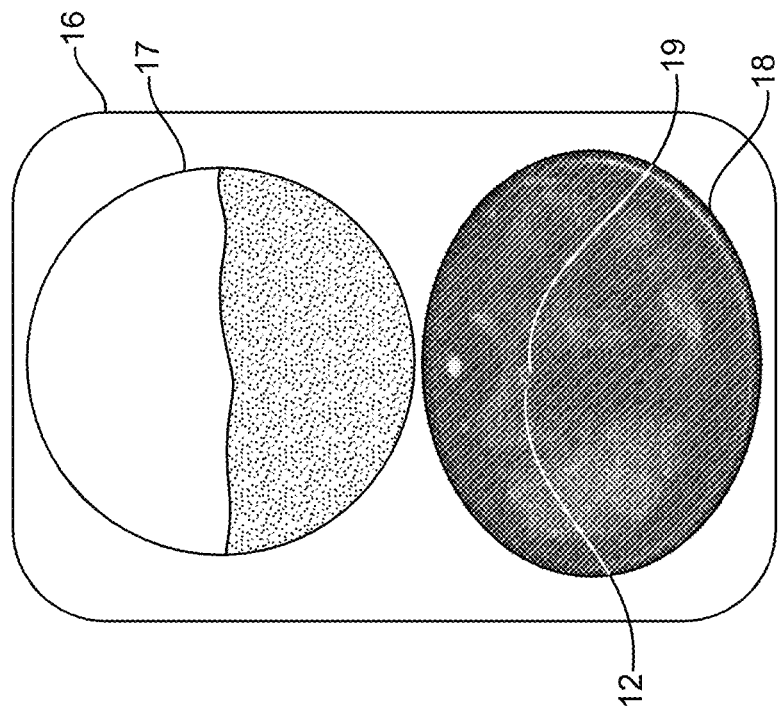
FIGS. 1A and 1B show the combined ultrasonic and visual hysteroscope inserted into the uterus, and the simultaneous images displayed on the video monitor.
Figure 1A:
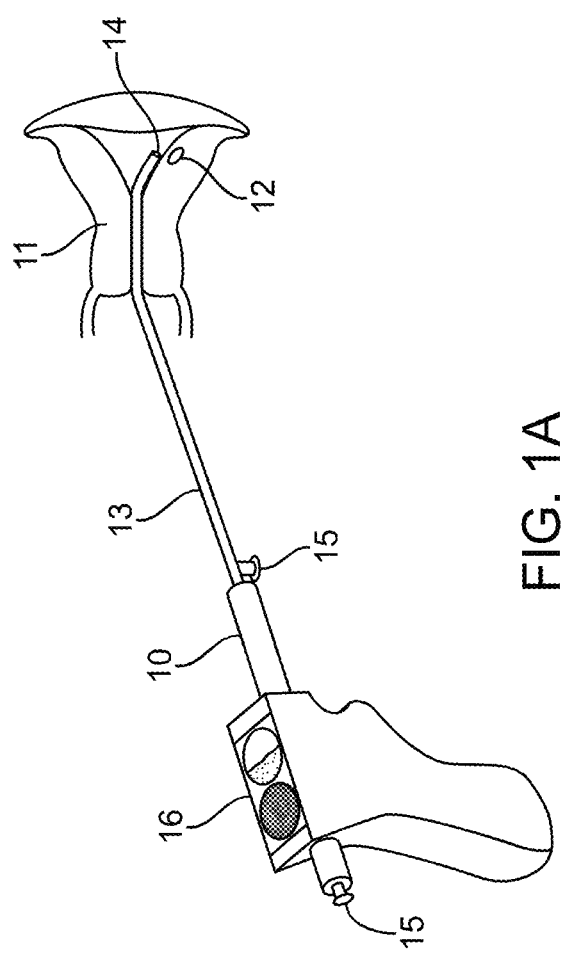

FIG. 1A illustrates the combined ultrasonic and visual hysteroscope 10 as it is inserted into the uterus 11. The cannula portion 13 of hysteroscope 10 contains a solid spherical distal lens 14 that allows visualization of both the uterine cavity, as well as tissue in contact with lens 14. This is not the case with conventional untipped endoscopes, which display a blurry image if the endoscope lens contacts tissue. An intramural fibroid lesion 12 is present within the muscular wall of uterus 11. Intramural fibroid 12 is not visible via endoscopic visualization, but it is visible via ultrasonic scanning. The combined ultrasonic and visual hysteroscope 10 incorporates the capability to deliver saline irrigation into the uterus 11, and to evacuate irrigation fluid and blood from the uterine cavity. Two female luer lock fittings 15 situated on the device allow attachment of an irrigation line and a suction line. A video monitor 16, generally a liquid crystal display (LCD) monitor, is incorporated in the device. The combined ultrasonic and visual hysteroscope device 10 is powered by a 9-volt battery, and the entire device is intended to be disposable after a single use.

FIG. 1B is an enlarged image of the video monitor 16, showing the simultaneous viewing of the endoscopic image 17 and the ultrasonic image 18. An indicator dot 19 appears on the ultrasonic image 18, and this dot 19 corresponds to the location of tip of the ablation needle that is advanced out of the ultrasonic and visual hysteroscope 10. Placement of the indicator dot 19 on the ultrasonic image 18 of the fibroid 12 aligns needle insertion with the fibroid 12 for ablation.

Figure 2C:
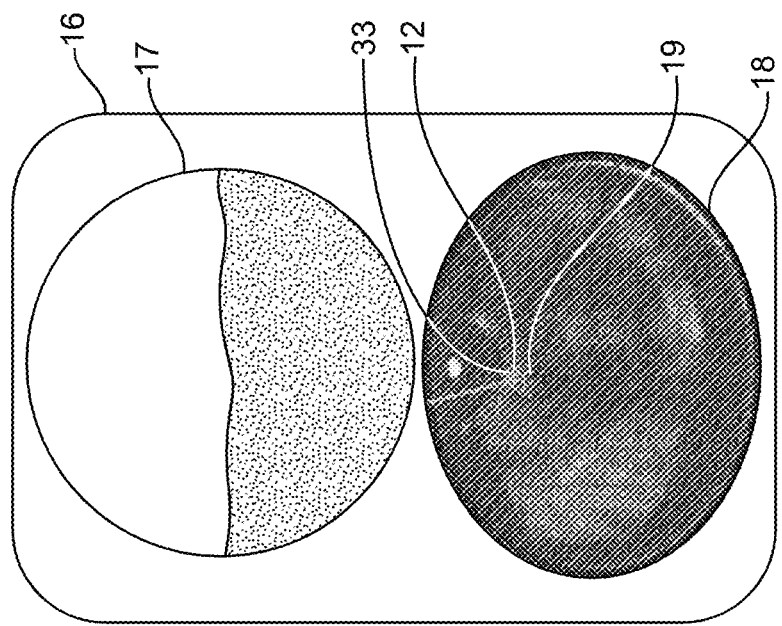
FIG. 2A-2C depict the combined ultrasonic and visual hysteroscope, the components comprising its cannula portion, including a multiple pronged ablation needle element, and the resultant images displayed on its video monitor.
Figure 2A:
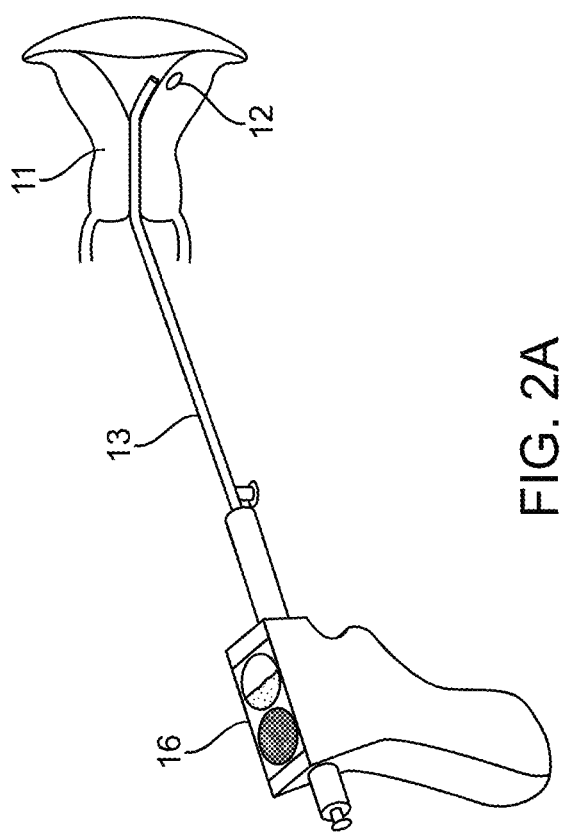
Figure 2B:
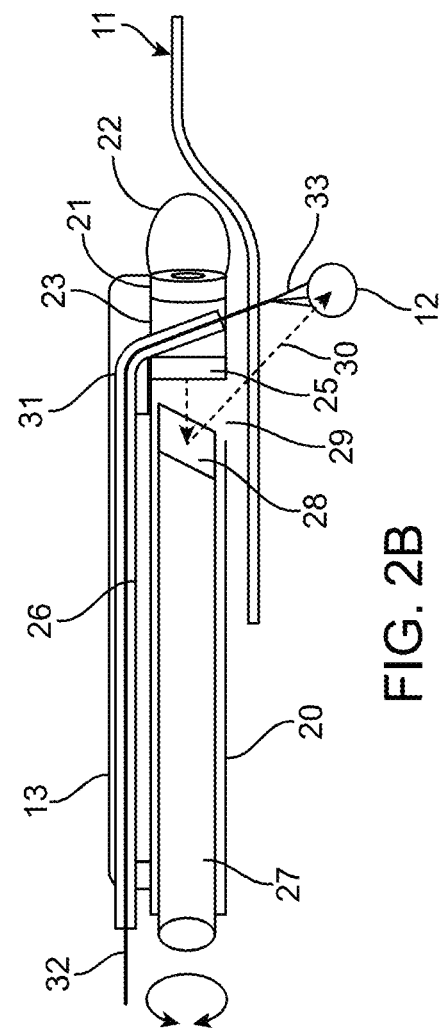

FIG. 2A is an illustration of the combined ultrasonic and visual hysteroscope 10 inserted into the uterus 11. FIG. 2B is a longitudinal sectional view of the cannula portion 13 of hysteroscope 10, depicting several of the components inside the cannula 13. A 3 mm diameter lumen 20 in the inferior aspect of cannula 13 houses an optical imaging element or CMOS chip camera 21 on its distal end. The CMOS chip camera 21 is bonded to a solid, optically clear spherical lens 22. The spherical lens 22 may be formed of a drop of ultraviolet light curable adhesive that is applied directly to the distal face of the CMOS chip camera 21, or it may be an injection molded polymer lens that is bonded with ultraviolet cure adhesive to the CMOS chip 21.

An ultrasound imaging element or ultrasound transducer 25 lies in the inferior lumen 20 of cannula 13, proximal to the CMOS chip camera 21. A 5 mm-7 mm gap lies between the CMOS chip 21 and the ultrasound transducer 25. The ultrasound transducer 25 faces in the proximal direction of cannula 13, such that its beam is directed inward in cannula 13, while the CMOS chip camera 21 views laterally outward from cannula 13. A rigid rod 27 with a distal angled reflective surface 28 lies approximately 10 mm-15 mm proximal to the ultrasound transducer 25, and the rod 27 rotates at a frequency of approximately 20-40 Hz. Ultrasound beams emitted from the transducer 25 strike the reflective surface 28 and exit via an opening 29 in the inferior wall of cannula 13. The reflected beams 30 image tissue beneath the endometrial surface of the uterus 11. Intramural lesions, such as a fibroid 12, may thus be observed via ultrasonic imaging.

A rigid angled tube 31 is positioned superior to the ultrasonic and video camera lumen 20, and the angled portion of tube 31 extends down to the inferior aspect of the cannula 13 in the gap between the CMOS chip camera 21 and the ultrasound transducer 25. Rigid angled tube 31 guides the forward advancement of a radiofrequency ablation element 32. Radiofrequency ablation element 32 is typically formed of super-elastic metal such as Nitinol, to enable it to accommodate passage through the angled portion of tube 31 and to extend straight downward to intersect with fibroid 12. A distal portion of the ablation element 32 may be formed as multiple needle segments 33 to diverge and engage a larger volume of the fibroid 12 for enhanced ablation energy delivery.

Also visible in the sectional view of cannula 13 are insulated wire conductors 23 and 26, that lie superior to inferior lumen 20. Wire conductor 23 enters a superior aspect of inferior lumen 20 at its distal end to supply power to the CMOS chip camera 21, while wire conductor 26 enters inferior lumen 20 at the site of the ultrasound transducer 25 to power that device.

FIG. 2C is an enlarged view of the video monitor image 16, depicting the simultaneous projection of the endoscopic image 17 and the ultrasonic image 18. Visible in the ultrasonic image 18 is the shadow of the multiple ablation needle segments 33, the fibroid 12 and an indicator dot 19 corresponding to the path of the main axis of the ablation element 32 as it extends laterally from cannula 13. During use of the combined ultrasonic and visual hysteroscope 10, the physician maneuvers the device to center the indicator dot 19 on the ultrasonic image of the fibroid 12, followed by targeted advancement of the ablation needle segments 33 into the body of fibroid 12.

FIG. 3A shows a longitudinal sectional view of the cannula 13, with the ablation element 32 lying inside the rigid angled guide 31, and the multiple needle segments 33 that comprise the distal end of ablation element 32. FIG. 3B depicts an embodiment of a configuration of the ablation element 32, with multiple wire elements 33 containing distal angled needle points and preformed bends 34 of the distal segment. The distal bent segment of wire element is approximately 2-3 cm in length. The entire length of the wire elements 33 proximal to the bend 34 may be constrained by an outer sheath 35 that maintains the orientation of the distal wire elements in a splayed out position. Outer sheath 35 may be composed of a heat shrink polymer such as polyolefin or polyethylene terephthalate (PET) that is shrunk around the bundle of wire elements 33 whose straight portions are attached together using ultraviolet cured adhesive. Alternatively, outer sheath 35 may be a metal tube formed out of a material such as stainless steel, with its outer surface insulated with a non-conductive polymer such as polyolefin, polyethylene or polytetrafluoroethylene (PTFE). FIG. 3C is a cross-sectional view of the straight section of the ablation element 32, composed of multiple strands of super-elastic wire 33 encased by an outer sheath 35. Each strand of super-elastic wire 33 may be approximately 0.5 mm in diameter, and the outer diameter of the ablation element 32 may be approximately 1.2 mm in diameter.

Figure 4C:
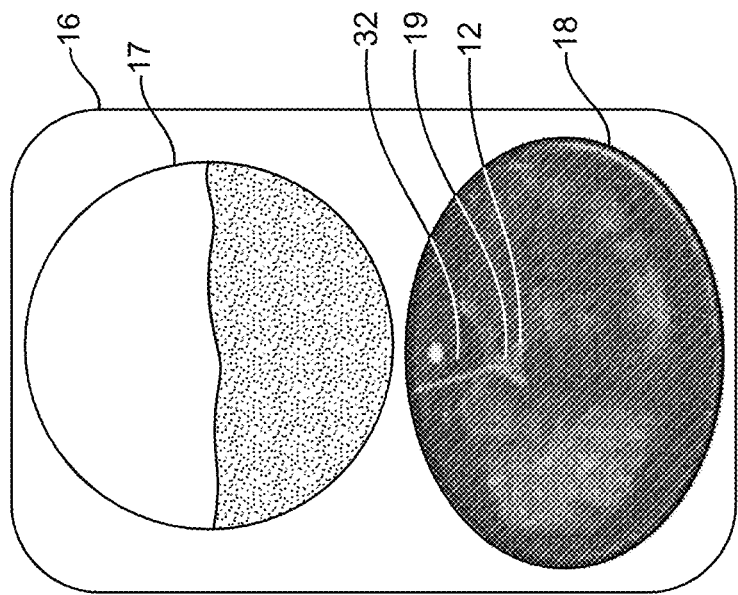
FIG. 4A-4C depict the combined ultrasonic and visual hysteroscope incorporating a single ablation needle element, and the resultant images displayed on the video monitor.
Figure 4A:
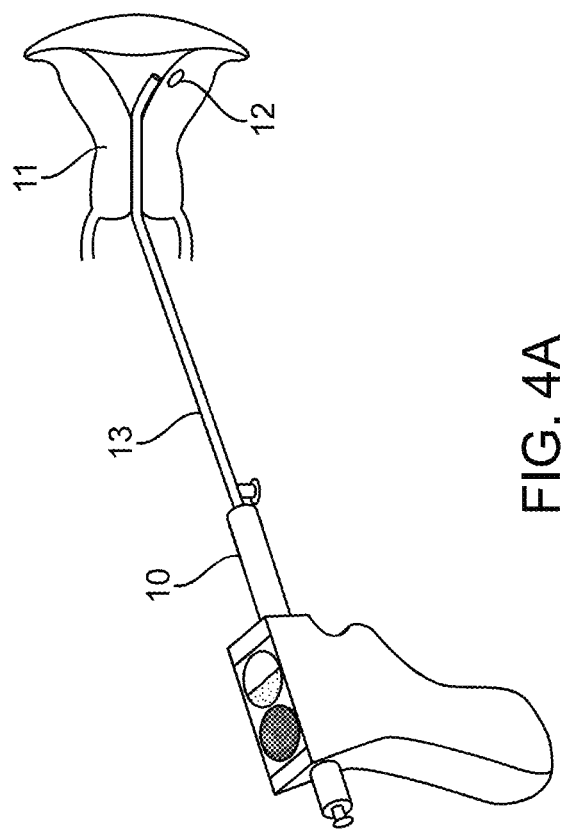
Figure 4B:
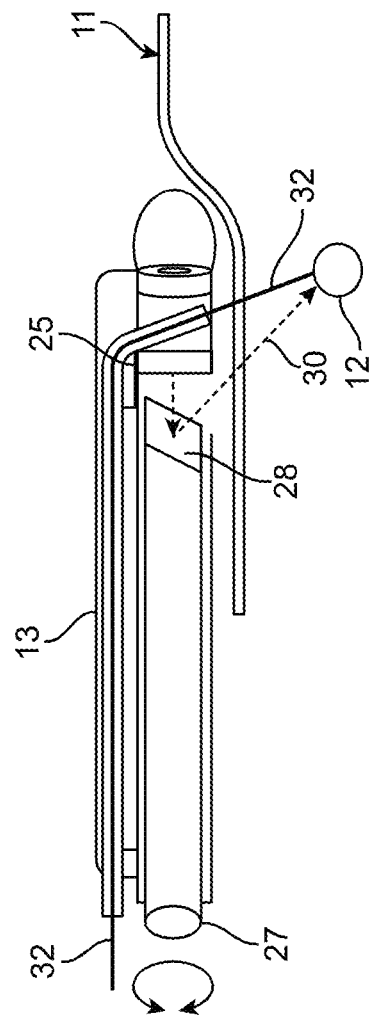

FIG. 4A depicts an alternate version of the combined ultrasonic and visual hysteroscope 10 inserted into the uterus 11. FIG. 4B is a longitudinal section of the device cannula 13, showing that the ablation element 32 in this version is comprised of a single solid super-elastic metal needle. When the hysteroscopic device 10 is used to ablate a large fibroid 12, the ablation element 32 is inserted and withdrawn multiple times in different regions of the fibroid 12 to perform the therapy. FIG. 4C is an enlarged view of the video monitor image 16, with the ultrasonic image 18 displaying the shadow of the single ablation needle element 32 as it enters the fibroid 12. The indicator dot 19 targets the entry location of the ablation needle 32 into the fibroid 12.

FIG. 5A is a side sectional view of cannula 13, depicting the inferior lumen 20 housing the ultrasound transducer 25 and the CMOS chip 21. Angled tube 31 lies superior to inferior lumen 20, and it houses ablation element 32 with its multiple distal needle segments 33. FIG. 5B is a cross-sectional view of cannula 13, showing the angled tube 31 and instrument channel 35 lying superior to inferior lumen 20. Two additional channels 35 lie lateral to angled tube 31 and instrument channel 35, to provide separate conduits for irrigation and suction during therapeutic uterine procedures. Also present in the FIG. 5A and FIG. 5B are the insulated electrodes lying in their own channels bounded by inferior lumen 20, angled tube 31, adjacent irrigation/suction channel 35; and inferior lumen 20, instrument channel 35, and adjacent irrigation/suction channel 35. One electrode 23 supplies power to the CMOS chip 21, and the other electrode 26 supplies power to the ultrasound transducer 25. Cannula 13 may be formed of individual semi-rigid metal or polymer tubes constrained together in the desired configuration using adhesive and an outer covering of heat shrink polymer, or it may be a multi-lumen extruded polymer tube with a short tubular section added between the ultrasound transducer 25 and the CMOS chip 21 to form the angled tube 31.

Figure 6:
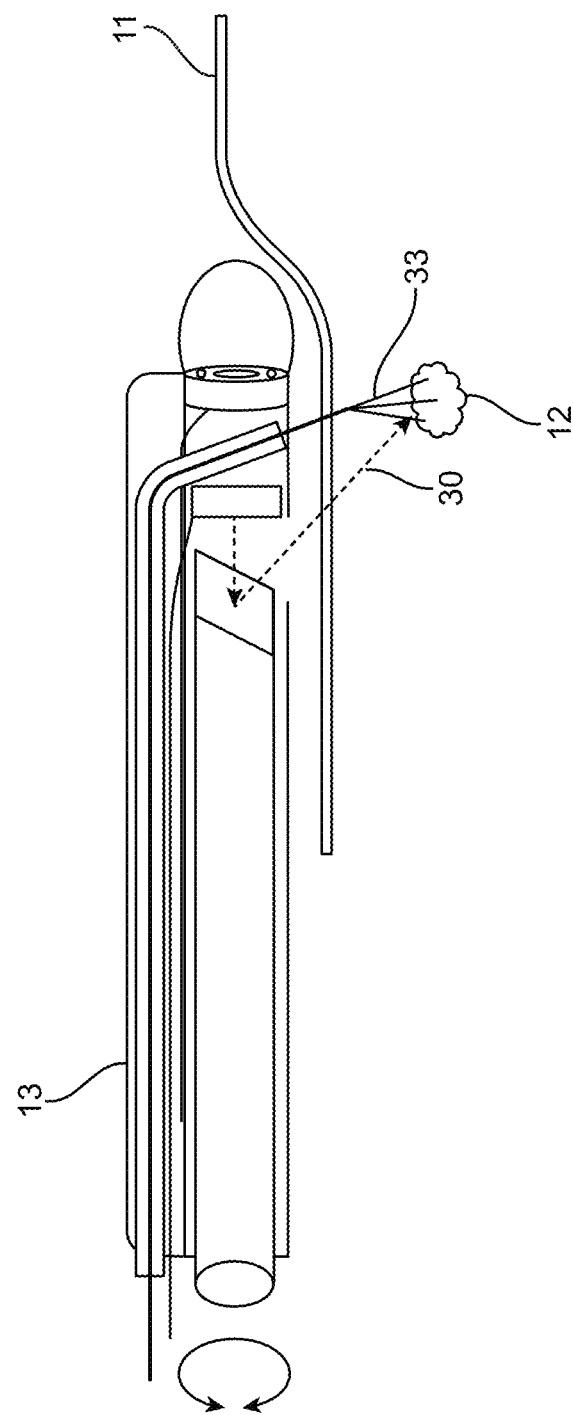
FIG. 6 shows a side view of the ultrasonic imaging path and the ablation treatment path intersecting at a location spaced laterally from the shaft of an example device in accordance with embodiments described herein.

FIG. 6 shows the path of the ultrasonic imaging beam 30 striking the target intramural fibroid 12 in the wall of uterus 11. The ablation treatment multiple needle component 33 may advance out of the cannula device 13 and the needle component 33 can intersect with the ultrasonic imaging beam 30 at the site of intramural fibroid 12.

Figure 7:
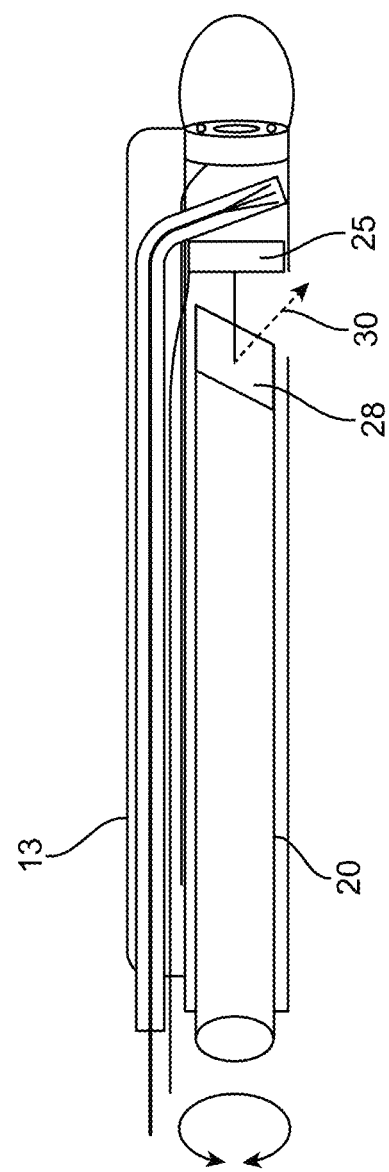
FIG. 7 shows a side view of the ultrasonic imaging element in tandem axial alignment with an example rotating reflective element in accordance with embodiments described herein.

FIG. 7 shows that both the ultrasonic imaging element 25 and the rotating reflective element 28 are situated in the inferior lumen 20 of the cannula 13 in axial alignment, such that ultrasonic beam 30 emitted by ultrasonic imaging element 25 can strike rotating reflective element 28 and may exit out of the side of cannula 13.

Figure 8:
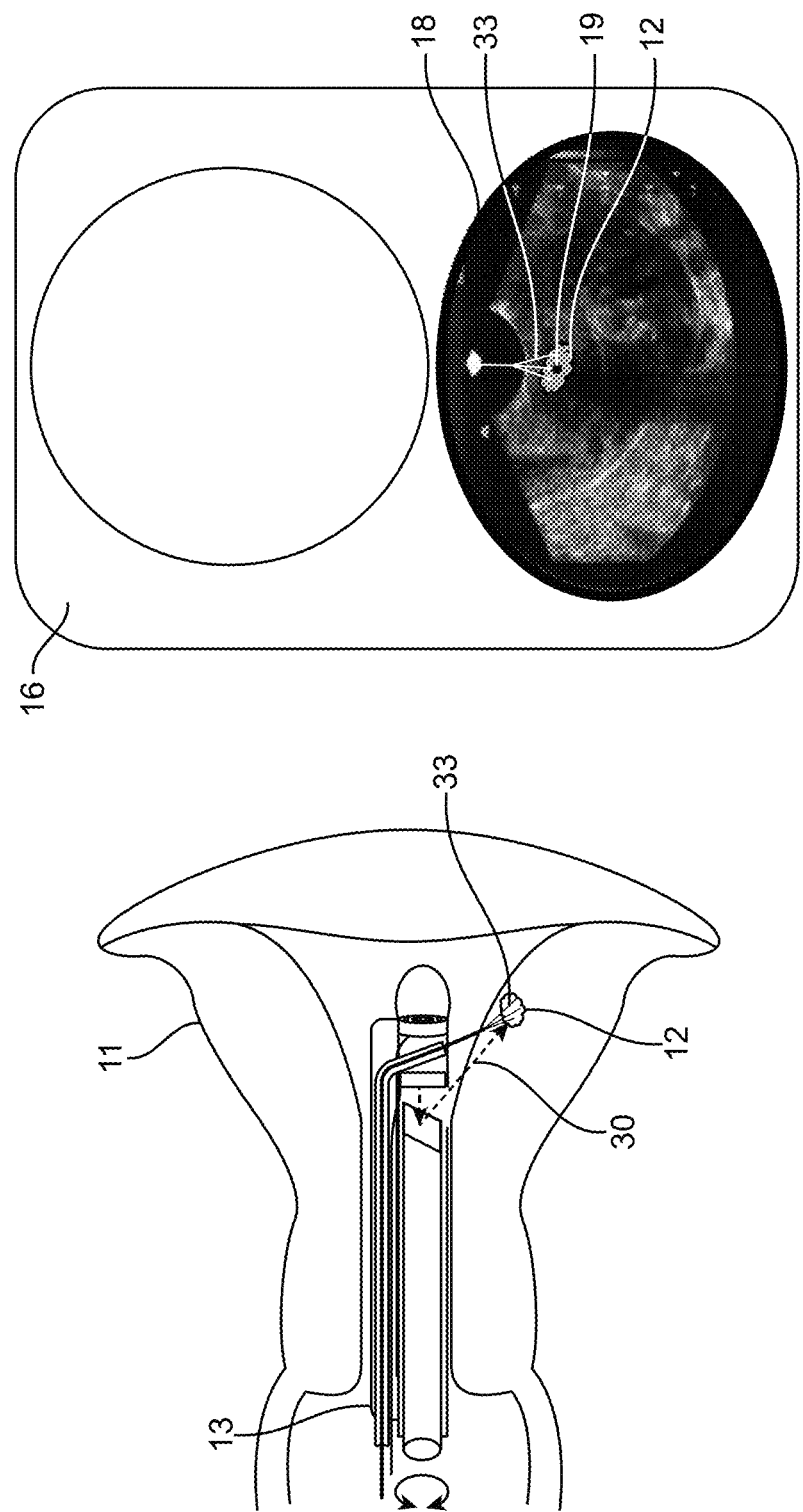
FIG. 8 shows a side view of the projected ablation treatment target location aligned with example anatomical structures observed in an example ultrasonic image as viewed top-down on an example device video monitor in accordance with embodiments described herein.

FIG. 8 shows the cannula 13 in an anatomical treatment position inside the cavity of uterus 11, with the corresponding ultrasonic image 18 visible in the device video monitor 16. When the indicator cursor 19 on the ultrasonic image 18 is placed in the center of the ultrasonic image of the intramural fibroid 12, advancement of ablation needle component 33 can be automatically aligned to intersect with the anatomic position of intramural fibroid 12, and images of both the ablation needle component 33 and its entry into the intramural fibroid 12 may be observed in the ultrasonic image 18 in device video monitor 16, which can assist proper ablation of fibroid 12 deep in the wall of uterus 11.

What is claimed is:
1. An interventional hysteroscope comprising:
   a cannula having a distal end, a proximal end, and a longitudinal axis therebetween;
   an optical imaging element at the distal end of the cannula;
   an ultrasonic imaging element at the distal end of the shaft cannula, said ultrasonic imaging element being configured to image along an image path;
   a treatment element configured to be deployed from the cannula along a treatment path, wherein the treatment element does not comprise the ultrasonic imaging element, wherein the imaging path and the treatment path intersect at an intersectional location spaced away from the cannula, wherein the treatment path and the imaging path are laterally oriented such that an angle between the treatment path or the imaging path and the cannula is between 45 degrees and 90 degrees; and a display configured to present both an optical image from the optical imaging element and an ultrasonic image from the ultrasonic imaging element;

wherein the display is further configured to present a marker on the ultrasonic image at a location corresponding to the intersectional location.

2. An interventional hysteroscope as in claim 1, further comprising a handle attached to the proximal end of the cannula.

3. An interventional hysteroscope as in claim 2, wherein the display is disposed on the proximal handle.

4. An interventional hysteroscope as in claim 1, wherein the optical imaging element comprises a solid-state camera.

5. An interventional hysteroscope as in claim 4, wherein the solid-state camera is attached to a spherical lens.

6. An interventional hysteroscope as in claim 1, wherein the ultrasonic imaging element is in tandem with a rotating mirror that reflects the outgoing and incoming ultrasonic energy laterally relative to the longitudinal axis of the cannula.

7. An interventional hysteroscope as in claim 1, wherein the treatment element comprises a superelastic needle.

8. An interventional hysteroscope as in claim 7, further comprising a needle lumen having a laterally deflected distal portion relative to the longitudinal axis of the cannula, wherein the superelastic needle is slidably mounted in the lumen so that a distal portion of the needle deflects laterally relative to the longitudinal axis of the cannula as the needle is advanced longitudinally through the lumen.

9. An interventional hysteroscope as in claim 7, wherein a distal end on the superelastic needle comprises a diverging array of needle segments.

10. A method for deploying at least one needle in tissue, said method comprising:

positioning a distal end of a treatment element deployment cannula proximate a surface of the tissue, wherein the treatment element is provided by a device comprising an ultrasound imaging element and the treatment element, wherein the ultrasound imaging element is configured to image along an image path, wherein the treatment element is separate from the ultrasound imaging element and comprises at least one needle, and wherein the imaging path and the treatment path intersect at an intersectional location spaced away from the cannula, and wherein the treatment path and the imaging path are laterally oriented such that an angle between the treatment path or the imaging path and the shaft cannula is between 45 degrees and 90 degrees;

displaying a real time optical image of a surface of the tissue;

displaying a real time ultrasonic image of the tissue including an anatomical feature to be treated;

presenting a marker on the ultrasonic image at a location corresponding to the intersectional location;

aligning the marker with the displayed anatomical feature;

advancing the treatment element into the tissue while maintaining alignment of the marker with the displayed anatomical feature; and applying energy through the treatment element to treat the anatomical feature.

11. The method of claim 10, wherein the anatomical feature comprises a uterine fibroid.

12. The method of claim 10, further comprising capturing the optical image of the surface of the tissue with an optical imaging element.

13. The method of claim 12, wherein the device comprising the ultrasound imaging element and the treatment element further comprises the optical imaging element.

14. The method of claim 10, wherein applying the energy through the treatment element to treat the anatomical feature comprises ablating the anatomical feature.

15. The method of claim 14, wherein the anatomical feature is ablated with radiofrequency energy.

16. The method of claim 14, wherein the anatomical feature is ablated using the at least one needle.

17. The method of claim 16, wherein the anatomical feature is ablated using at least one diverging needle segment of the at least one needle.

18. The method of claim 10, wherein advancing the treatment element into the tissue comprises advancing the at least one needle laterally relative to a longitudinal axis of the treatment element deployment cannula.

* * * * *